(12) United States Patent
Hernandez Aguayo et al.

(10) Patent No.: US 8,609,361 B2
(45) Date of Patent: Dec. 17, 2013

(54) REAL TIME ELECTROPHYSIOLOGICAL TESTING OF AGENTS OF INTEREST FOR TREATMENT OF AMYLOID-TYPE DISEASES

(75) Inventors: Luis Gerardo Hernandez Aguayo, Concepcion (CL); Carlos Roberto Martinez Opazo, Concepcion (CL); Jorge Luis Rivera Parodi, Concepcion (CL)

(73) Assignee: Universidad de Concepcion, Concepcion (CL)

( * ) Notice: Subject to any disclaimer, the term of this patent is extended or adjusted under 35 U.S.C. 154(b) by 403 days.

(21) Appl. No.: 12/682,230

(22) PCT Filed: Oct. 9, 2008

(86) PCT No.: PCT/EP2008/063528
§ 371 (c)(1),
(2), (4) Date: Aug. 4, 2010

(87) PCT Pub. No.: WO2009/047288
PCT Pub. Date: Apr. 16, 2009

(65) Prior Publication Data
US 2010/0311102 A1 Dec. 9, 2010

(30) Foreign Application Priority Data
Oct. 9, 2007 (CL) .................................. 2908/2007

(51) Int. Cl.
*C12Q 1/02* (2006.01)
(52) U.S. Cl.
USPC .......................................................... 435/29
(58) Field of Classification Search
None
See application file for complete search history.

(56) References Cited

U.S. PATENT DOCUMENTS

| | | | |
|---|---|---|---|
| 5,580,748 A | 12/1996 | Alkon et al. | |
| 6,107,050 A | 8/2000 | Alkon et al. | |
| 6,172,043 B1 | 1/2001 | Ingram et al. | |
| 6,942,963 B1 | 9/2005 | Ingram et al. | |
| 6,960,470 B1 | 11/2005 | Malinow et al. | |
| 7,101,879 B2 | 9/2006 | Ingram et al. | |
| 2002/0102553 A1 | 8/2002 | Coleman et al. | |
| 2003/0211542 A1* | 11/2003 | Lee et al. | 435/7.1 |
| 2005/0084875 A1 | 4/2005 | Coleman et al. | |
| 2006/0053499 A1 | 3/2006 | Kretzschmar et al. | |

FOREIGN PATENT DOCUMENTS

| | | |
|---|---|---|
| EP | 1 292 187 | 4/2006 |
| WO | 92/02248 | 2/1992 |
| WO | 98/43094 | 10/1998 |
| WO | 99/35501 | 7/1999 |
| WO | 02/059619 | 8/2002 |
| WO | 2004/064768 | 8/2004 |
| WO | 2004/093830 | 11/2004 |
| WO | 2006/052691 | 5/2006 |
| WO | 2006/053787 | 5/2006 |
| WO | 2006/004194 | 12/2006 |

OTHER PUBLICATIONS

Pasquet et al, Eur J Biochem 239: 647-54, 1996.*
Priel et al (Bioph J 92:3893-3900, 2007.*
Hamill et al , Pflüger Arch 391:85-100, 1981.*

* cited by examiner

*Primary Examiner* — Lei Yao
(74) *Attorney, Agent, or Firm* — Shaukat A. Karjeker; Colin P. Cahoon; Carstens & Cahoon, LLP (57) ABSTRACT

This invention corresponds to an in vitro method that employs an electrophysiology technique; in particular, an embodiment of the patch-clamp technique in its perforated type, which will allow us evaluating the neurotoxic capacity of protein structures associated to the generation of neurodegenerative diseases. It addition, it allows evaluating potential pharmacologic capacities of candidate molecules (drugs) in order to prevent, treat, or cure the said diseases. The invention involves the use of peptides that cause neurodegenerative diseases in order to form a spontaneous perforated recording that only occurs with peptides in the patch clamp glass pipette.

9 Claims, 3 Drawing Sheets

REAL TIME ELECTROPHYSIOLOGICAL TESTING OF AGENTS OF INTEREST FOR TREATMENT OF AMYLOID-TYPE DISEASES

This invention corresponds to an in vitro method that employs an electrophysiology technique; in particular, an embodiment of the patch-clamp technique in its perforated type, which will allow us evaluating the neurotoxic capacity of protein structures associated to the generation of neurodegenerative diseases. It addition, it allows evaluating potential pharmacologic capacities of candidate molecules (drugs) in order to prevent, treat, or cure the said diseases. The invention involves the use of peptides that cause neurodegenerative diseases in order to form a spontaneous perforated recording that only occurs with peptides in the patch clamp glass pipette.

DESCRIPTION OF RELATED ART

Neurodegenerative diseases, together with vascular and oncological diseases, are important public health problems due to their relevance and impact on the population, as they have become main causes of morbidity and death. This has led the pharmaceutical industry to research on the development of drugs and treatments for the said disorders.

Two decades ago, little was known about the causes of neurodegenerative diseases. However, it is clear now that they are the result of anomalies in the processing of certain proteins which, when accumulated in nerve tissues, within and outside the neurons, cause clinical symptoms that can be identified and distinguished. In these diseases, clinical and progressive processes are evidenced, characterized by selective and asymmetric loss of neurons in the motor, sensorial, and cognitive systems.

In the particular case of neurodegenerative diseases, their effect on the population has clearly increased during the last years, mainly triggered by life expectancy increase. In particular, said increase has resulted from senior citizens being the age group that increased most during the last decade. This is reflected in the alarming aging of the population, especially in western countries, where citizens' life expectancy has increased, mainly as a result of preventive and curative medicine with regards to other types of disorders, such as infections.

Statistics indicate that average life expectancy in the USA will be 80.5 years in 2050. At the same time, it is estimated that, for children born in 2050, life expectancy will be 90.9 years in Japan and 82.9 in the USA (Tuijapurkar et al., 2000).

Currently, in the United States there are around 4 million patients who suffer from Alzheimer, and this is expected to increase to more than 16 million by 2050.

It is clear that we are witnessing a social phenomenon that will impose important modifications to individuals' relations in any western country and its local health authorities with regards to health habits and concern. It is expected that medical problems of older individuals will affect every tissue and system in their bodies; however, it is the brain and its aging that should be of greater concern.

It could be said that the aging process is the result of the individual's genetic background combined with the environment where he/she lives. Currently, it is known that neurons of a young adult do not generally die in the brain cortex, although this does happen in other areas of the brain and, together with this, new neurons are generated in some areas of the brain. Studies on animals indicate that these phenomena are conditioned by the environment in which the individual lives (Mora, 2001).

Progressive increase of life expectancy in western countries draws more and more the attention of authorities and health and medical companies towards the pathologies affecting individuals of advanced age. Therefore, the population massive and progressive aging has become a very important risk factor in disease impact, such as Alzheimer and Parkinson.

In the particular case of Alzheimer Disease, it is estimated that around 10% of 65 year olds are affected in a certain degree by this disease, which progressively increases with age, and it becomes 50% for population over 85. Alzheimer Disease is hereditary or sporadic. In the first case, it appears in around 10% of cases; it may appear at early age with severe symptoms. When sporadic, i.e. in patients with no disease background, it accounts for 90% of cases.

This pathology results from changes in the brain of people who suffer it. In the patients' brain tissue it is possible to observe neuron degeneration on areas related to long and short memory. Degeneration includes selective death of nerve cells, loss of synapse, and a decreasing in certain neurotransmitter levels. Other alterations typical of the disease are the presence of two types of protein aggregates known as neuronal tangles and senile plaques. Neuronal tangles are formed by bundles of paired filaments in helicoidal arrangement, mainly made by a cytoskeleton protein known as Tau and enriched in phosphate groups. On the other hand, senile plaques are formed in their periphery by degenerating neuron prolongations (dendrites and axons) and in its center by amyloid fibrils. The amyloid fibril main component is a 6 to 10 nm long filament formed by identical β-folded sub-units arranged as anti-parallel called β-amyloid (Aβ).

Evidence suggesting that Aβ peptide deposit is the main event triggering the Alzheimer Disease process is varied and conclusive. Aβ peptide is found in the form of fibril aggregates in amyloid deposits, as well as circulating in a soluble form in plasma and cerebrospinal fluid of normal individuals and of those affected by this disorder.

Therefore, Aβ peptide has an enormous relevance and significance in the evolution and generation of Alzheimer Disease; for this reason, many studies focused on this disease aim at designing strategies in order to inhibit the formation of amyloidogenic deposits. Said studies evaluated the characterization and intervention by which the amyloid negative effect on the brain could be blocked, for instance, by inhibiting the expression of the gene that codifies amyloid precursor protein (APP); by decreasing APP processing that originates Aβ; by blocking amyloid formation and deposit; by helping amyloid elimination from the brain, and by preventing the amyloid toxic effect.

According to the above, development of experimental models to evaluate, understand and explore neurodegenerative disorders is a highly necessary tool to better develop treatment methods for the said pathologies. These models have been developed in different ways and have originated different options to understand neuro-pathologies. Among them, Alzheimer Disease has been a large focus of attention.

In vitro models have been developed in order to evaluate the effect of candidate molecules inhibitors of neurodegenerative disorders, such as Alzheimer Disease. WO 2006036637 describes an assay for potentially benefical drugs against atherosclerosis, cancer and Alzheimer's disease, and their effectiveness in vitro, wherein the assay comprising a system where LDL or cholesterol is given to cells together with the drug being tested and then chromosome segregation and aneuploidy are detected using probes specific for targeted chromosomes. On the other hand, US 2002102553 and US 2005084875 publish a method to determine markers and sensitivity by quantifying anti-sense mRNA.

A different approach is noticed when cell cultures are used to evaluate culture viability. In WO 9843094, study and identification of agents capable of reducing Aβ in brain cells are carried out. A similar proposal is addressed in EP 0541686, where an in vitro method is published to identify candidate molecules in neuron cell culture, capable of inhibiting Aβ derivatives neuro-toxic effect.

Another group of available developments is focused on the study of alterations in protein binding, and how this is affected through the use of candidate molecules when treating neurodegenerative disorders. In WO 2006004194, a method to identify candidate molecules affecting the TGF ss2 and APP binding in cells expressing APP is described. In an equivalent way, WO 9935501 publishes a method to identify substances that alter interaction with preseniline, useful to test the presence of preselinine alleles in individuals with, or with a tendency to Alzheimer Disease or related disorders. In this same sense, U.S. Pat. No. 6,960,470 describes an in vitro "screening" method to detect candidate drugs for Alzheimer treatment. The method employs mammalian hippocampal cell tissue cultures with a mutation in the preselinine gene with an increased synaptic boost on a stimulus, compared to wild-type cells, due to a modification of the GABA reuptake route. Synaptic response is evaluated through measurements with patch clamp.

The patch clamp technique has been used for diagnosis and screening in drugs that are therapeutically effective in neurodegenerative pathologies. This is the case of document U.S. Pat. No. 5,580,748 that described a method for Alzheimer diagnosis by detecting differences between potassium channels in patients with Alzheimer Disease and normal donors with regards to intra-cellular calcium and its response to known compounds that increase intra-cellular calcium levels. In addition, it is possible to find that U.S. Pat. No. 6,107,050 describes a method that uses β-amyloid peptide differential effect on the PKc-alpha and PKC-gamma kinase protein levels in Alzheimer patients' cells and in normal patients' cells.

On the other hand, U.S. Pat. Nos. 6,942,963 and 6,172,043 describe a mechanism to identify β-amyloid peptide cytotoxicity, which would allow treating symptoms triggered by the aggregation of β-amyloid peptide by administering an active ingredient antagonizing the neuro-toxicity mechanism. Through this process, pharmaceutically active peptides are identified. Also, U.S. Pat. No. 7,101,879 establishes that, when searching for compounds that inhibit fluorescence increase associated to de-polarization or increase of intra-cellular calcium, anti-Alzheimer drugs could be obtained. However, this technique causes complications in the understanding of the peptide action, as the fluorescence associated to calcium is not specific because it is produced by multiple mechanisms; therefore, said technique does not aim at the peptide action on the membrane. Also, fluorescence changes may not be associated to de-polarization. On the other hand, the perforated technique developed in this document may be used with much higher accuracy on a single cell, new automatized methodologies will allow performing this analysis in parallel on multiple cells.

There are indirect methods to determine neuro-degenerative disorders; for instance, WO 02059619 describes an in vitro method to determine disorders associated to protein glycolization by joining blood extract with wheat germ.

A different solution is the development of animals, preferably transgenic mammalians, in order to study neuro-degenerative disorders, such as Alzheimer Disease, or to evaluate the efficiency of candidate molecules in their treatment. This is the case of Perdita L. Pugh et al. (Behav Brain Res. 2007. Jan. 15; 17229472), WO 2006053787, WO 2006052691, EP 1292187, US 2006053499, WO 2004064768 or EP 1608962, among other.

The use of electro-chemical techniques for this study of physiological properties in cells is well known. In fact, voltage clamp electrophysiologic recording techniques ("patch-clamp") allow studying the properties of ionic resistance flowing through different ionic channels in the plasma membrane in isolated cells with regards to those coupled to receptors (nicotinic, $GABA_A$), as well as to those voltage-operated ($Na^+$, $Ca^{2+}$, $Cl^-$ and $K^+$ channels, mainly). Thanks to the patch-clamp techniques' different configurations (attached patch, whole cell, isolated patch), it is also possible to know how the intimate action mechanism of a given chemical entity (neuro-transmitter, peptide, drug) affects opening and closing kinetics of a given ionic channel. These methodologies are highly useful in order to characterize a drug action mechanism that may condition its use, efficiency, and safety at the clinic, such as calcium antagonists with therapeutic applicability in different cardiovascular pathologies, or drugs with neuronal nicotinic receptor agonist activity and therapeutic potential in the treatment of Alzheimer Disease.

Therefore, this invention provides a technical solution through patch-clamp electro-physiologic recording techniques, allowing a electro-chemical, fast, sensitive, and simple method that allows identifying, in real time, microscopic alterations suffered by neurons due to the action of aggregated proteins that modify the cellular membrane electric stability. Clearly, the said development is not related to said state-of-the-art, as measurements taken are different; it is a different detection strategy, highly sensitive, and a better alternative for the development and evaluation of new candidate molecules to treat neurodegenerative diseases.

DESCRIPTION OF THE FIGURES

FIG. 1A shows an electrophysiologic recording when a cell is exposed to Aβ. It shows a typical high-resistance seal immediately after establishing the configuration known as "cell attached". With time, Aβ aggregates (500 nM) in the glass pipette solution spontaneously convert the recording into a perforated variation of the technique, shown through increased capacitative peak and late conductance. FIG. 1B shows the development of a typical perforation with the anti-biotic gramicidin (50 μM) in the glass pipette. In absence of Aβ or gramicidin, cell attached recordings are stable for more than 60 min.

FIG. 2A is a graph indicating the Aβ peptide aggregation structure progress in solution. Its shows the turbidity changes in a solution with amyloid peptide that indicates Aβ peptide aggregation to the solution. This measurement was carried out in a phosphate buffer solution at 7.4 pH at 100 μM Aβ concentration, under sterile conditions, at 37° C., and stirring at 300 rpm. The solution absorbency measurement is observed as a change in optical densities (D.O.), which reflects formation of complex structures, amyloid aggregates. Images B-D correspond to ultra micro photographs obtained with an electronic microscope. The recognition of different structures formed during the aggregation process is possible. Aggregates obtained at 120 min and fibers obtained at 5 days of aggregation are readily noticed.

Control is the charge in cell-attached configuration and reflects the recording of the glass pipette properties partially compensated to visualize part of the transient. Negative pressure reflects the charge obtained with a routine whole-cell configuration. Gramicidin and amphotericin are antibiotics routinely used to generate perforates. Data are ±S.E. average (n=6; different experiments).

DESCRIPTION OF THE INVENTION

This invention is related to an in vitro electro-chemical procedure to evaluate the neuro-toxic capacity of protein structures in living cell plasma membranes. This means that this invention, through the analysis of changes in the capacitative (or resistance) peak kinetic form—which demonstrates changes in the membrane conductance—allows recording the protein aggregates' interaction, such as amyloids, with biologic membranes. In one of the invention embodiments, it shall be possible to search for molecules (drugs) that interfere with the formation of pores detected with the methodology and allow a unique and new form of interfering in the degenerative process.

In a preferable embodiment, this refers to a process employing a high-sensitivity electro-physiologic analysis in order to evaluate the neuro-toxic capacity of protein structures associated to disease or neurodegenerative disorders in mammals, as well as pharmacologically active properties in molecules that may interfere with, or block said processes. Particularly, the phenomena under study are cellular membrane alterations related to Alzheimer Disease. This method will allow identifying molecules or procedures to block neuro-generative peptide effects, such as Aβ and other peptides involved in Parkinson, amyotrophic lateral sclerosis, and Huntington.

The invention procedure uses the patch-clamp technique, which allows studying electric properties of biologic membranes in live cells. In the invention procedure, fine electrodes are used to evaluate and record electro-physiologic modifications that occur in cell membranes as a result of different stimulus and conditions, as may be the effect of proteins, active ingredients, or candidate compounds to treat different pathologies or neurodegenerative disorders. In a preferable embodiment, this invention involves electro-physiologic measurements that are not related to calcium influx or membrane de-polarization.

The invention procedure allows studying and recording properties of mammalian cell cultures in the plasma membrane in order to quantify protein molecules and/or pharmacologically active molecules' toxic effects in real time. In one embodiment, the effect of these molecules on aggregate proteins that cause neurodegenerative diseases such as Alzheimer Disease, Parkinson Disease and amyotrophic lateral sclerosis are studied and recorded. In a preferable embodiment, the invention is addressed to the toxic effect caused by the β-amyloid peptide action (Aβ), the main neurotoxic agent associated to the Alzheimer Disease.

In an invention embodiment, it is described that Aβ peptide quickly affects (in a few minutes) electro-physiologic properties of membranes due to the aggregates action on the cell membrane; this way, a modification is generated in cell ionic homeostasis that would lead the cell to disconnection and later death. Therefore, said electric changes, associated to changes of small pA range, caused by the Aβ peptide, provides the possibility of quantitatively measuring the alteration of biologic membranes exposed to synthetic or natural Aβ peptide aggregates; i.e. this invention is aimed at recording fast conductance change signs that are not calcium influx detectable through other methodology or de-polarization. Therefore, changes recorded by the invention are related to the integrity modification of the lipid membrane resulting from protein aggregation caused by Aβ and forming of the amyloid pore. These changes provide evidence with regards to peptide aggregation perforating the cell membrane, which initiate the neuro-degeneration processes.

In the invention embodiment, this procedure allows seeking and evaluating active and/or compound principles of pharmacologic interest inhibiting the protein structures interaction with biologic membranes, associating this action to the generation of neurodegenerative diseases or disorders. The invention corresponds to a method performed through a specific procedure, or high sensitivity, during early response stages, in real time, and before any sign of calcium influx or membrane de-polarization. This invention provides a methodology that allows seeking and evaluating active and/or compound principles of pharmacological interest that inhibit Aβ peptide effects by preventing the forming of structures that interact with the membrane, inhibiting the structures interaction with the membranes, or blocking the effect of structures that interact with the membrane, among other processes. This procedure provides an innovating tool to design neuro-protector molecule development useful for the treatment of Alzheimer Disease.

Additionally, this procedure allows a quick and quantitative evaluation of potential active and/or compound ingredients that may become neuro-active compounds of neuro-toxic or therapeutic application. In particular, this invention is advantageous with regards to other methods, such as fluorometric study, which is a method useful in the research of macroscopic effects that records later signs caused by peptide aggregates on membranes. Quite the opposite, this invention allows studying in detail the fine interaction described with regards to molecules of interest with biologic membranes, with no need for modification or implementation of new electro-physiologic technologies for its execution.

In fact, the invention allows examining and recording the molecules interaction with cell membranes without considering possible de-polarization effects caused by the peptide, which is a complex and non specific response. In fact, in measurements taken with this invention method, no de-polarization in the presence of peptide has been detected. In the whole cell embodiment, the invention records measurements with patch clamp that have not shown significant changes in membrane potential at low concentrations (preferably less than 1 μM and more preferably of 0.5 μM Aβ). However, the method described herein allows detecting conductance changes at said concentrations which, no doubt, refer to the method higher sensitivity compared to other measurement forms, such as membrane potential or fluorometry for calcium. This is because changes in ion flow through amyloid pores are too small as to produce variations in the membrane potential, although conductance modifications are generated in the membrane as a result of neuro-toxic complexes.

The experimental evidence of the invention allows establishing that conductance changes may be the result of the forming of a cationic-type pore, very similar to that generating gramicidin. In experiments where the Aβ effect is compared to gramicidin or amphoterecine, ionspheres for cations and anions, respectively, it is found that the peptide effect is similar to gramicidin, with this supporting the idea that peptide generates pores that allow cation influx (calcium, sodium). Because low-concentration peptide only forms a few pores in the cell, the current range is of a few pA (≤50 pA), which shows that the invention develops an ion flux recording method in a small membrane area; therefore, the invention is not a de-polarization or evoked current type.

i. Basically, this invention procedure is formed by two stages:
    b) Exposing a small area or patch of plasma membrane, in a preferable embodiment said membranes are neuron membranes, to peptide aggregates under study and/or to active ingredients, and/or compounds of interest.
    c) Determining, measuring, and quantifying electric parameters of membranes exposed to these aggregates; in a preferable embodiment, the parameter is conductance (inverse of electrical resistance resulting from resistance range and the glass pipette potential).

The method described in this invention detects previous events much earlier than any calcium influx that may be monitored, in addition to recording and measuring in the absence of membrane de-polarization. Therefore, this invention is technically different from the usual fluorometric or patch-clamp methods, discarding the use of membrane de-polarization by Aβ peptide, which has not been detected during this invention measurements and recordings.

Figure 1:
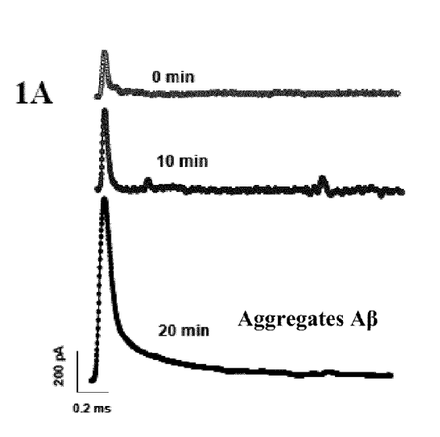

In fact, this invention method allows measurements and recordings that electrically detect the forming of the amyloid pore, a sign that is significantly more sensitive than a membrane potential variation. This is reflected in FIG. 1, where gramicidin and amyloid effect potencies is compared.

In an embodiment, the method described in this invention is useful for the study of very small peptide effects (slight, of low significance), preferably Aβ aggregation, in cell membranes, as well as of molecules that may interfere with said effects. Therefore, the method published herein is significantly different from art descriptions where the so called whole-cell form has been used. In the said art descriptions, studying the Aβ peptide effect on the entire cell membrane extension and recording membrane potential or resistance changes is possible. Due to the considerable extension of the membrane observed using said known method, small signs cannot be detected due to its electric noise (10-50 pA, 10 or more mV) coming from thousands of ionic channels in the cell under study.

Figure 2:
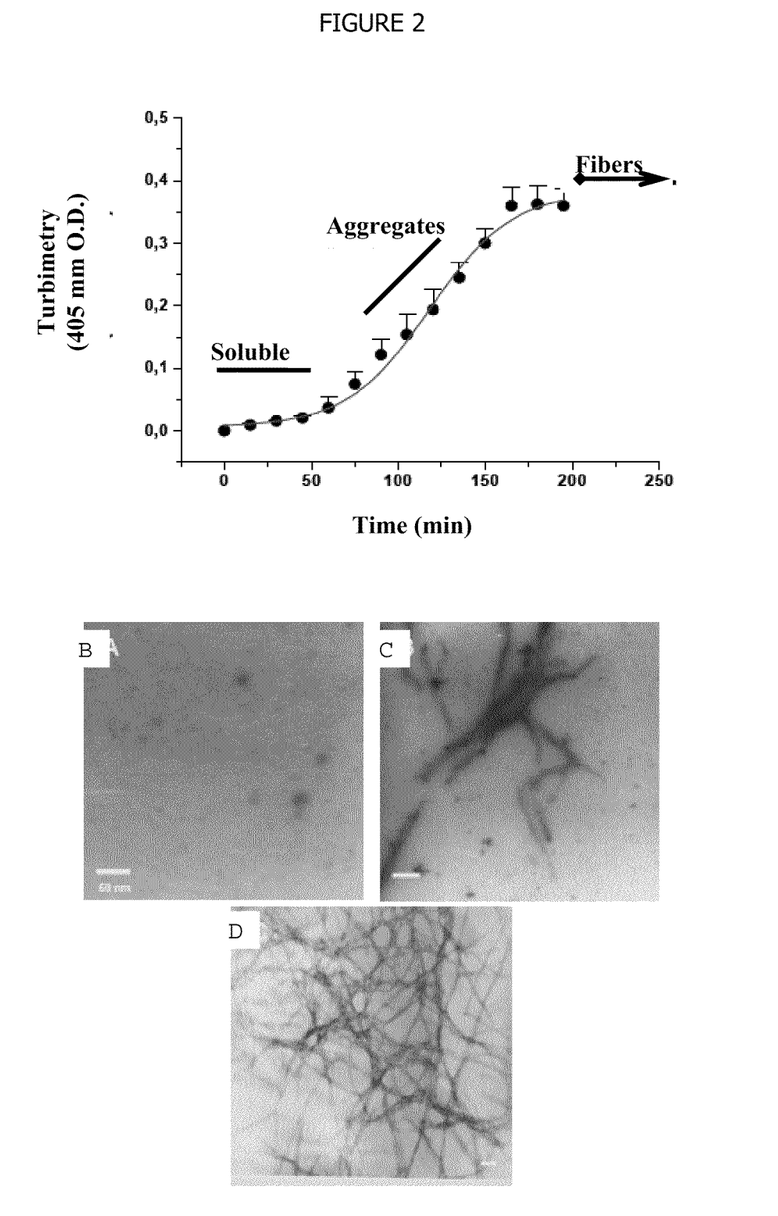
Figure 3:
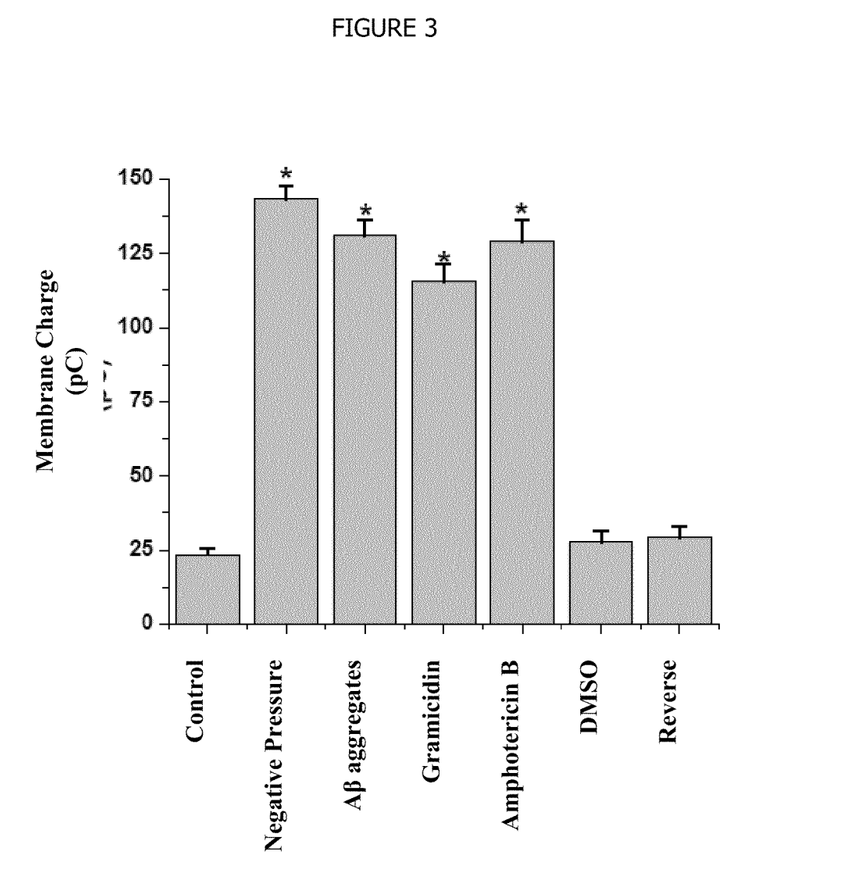
FIG. 3 shows a graph where the charge transferred by the cellular membrane during a 10 mV pulse and under different conditions was measured, and demonstrates the capacity of Aβ peptide aggregates to form perforations in the membrane.

The method described in this invention uses a variation of the technique known as patch cell-attached to study the Aβ peptide effects. In this invention embodiment, records very stable in time are obtained and maintained for more than 5 minutes, preferably for more than 15 minutes, and more preferably for more than 30 minutes. At the same time, this embodiment provides an intrinsic noise level under 5 pA, preferably under 3 pA, and more preferably under 1 pA, which may be due to the registry being obtained from a small cell area that normally contains very few ionic channels. In the invention method, and following the high-resistance seal formation, input current varies between −40 to −70 pA, preferably around −50 pA (negative) in the presence of Aβ, which demonstrates the formation of cationic pores. However, the most important characteristics in this event is the evidence of the fast capacitative resistance component, which reflects formation of a perforated form that supports the conclusion that pores are generated in the membrane (see FIGS. 1 and 2).

This invention provides a recording method carried out at a stable resistance level, which is of great importance and highly favorable when establishing basic control conditions, critical for the invention application, as only Aβ peptide application in the recording system, such as the glass pipette, causes a small increase of ionic resistance, depending on time and concentration, under the patch being recorded. Under these conditions, a spontaneous transition occurs in the recording that goes from cell-attached to perforated embodiment. This change reflects, as an expert in the art knows well, the incorporation of conductance pathways (pores or channels) in the membrane caused by the Aβ peptide. According to this information, these pores would produce strong changes in ionic homeostasis and later the death of neurons. Therefore, this invention represents the only way described to monitor this effect quickly and efficiently before the ionic homeostasis change and cell deterioration.

Furthermore, the invention herein is an important advancement compared to previous studies described in the art, as conductance generation in cell attached configuration is the basis for changes usually recorded as de-polarization and increase of fluorescence for calcium. It has been reported that peptide effects on calcium levels are inhibited by CNQX and DL-P5, which highly suggests a peptide effect on AMPA and NMDA receptors. Different from the above, this invention is fully independent from membrane receptors, for which reason it mainly reports the lipid membrane conductance state without the recorded resistance being modified by ionic events. In addition, an expert on the art may realize that the membrane de-polarization phenomenon is not fully accurate and it is not fully correlated to calcium fluorometry, as this ion may be modified as a result of its release from intra-cell locations.

At the light of this invention, a molecule able to inhibit conductance changes would be an excellent candidate to become an anti-Alzheimer drug, granting this invention the quality to be used as a screening method for the identification of anti-neurodegenerative active molecules. Also, it is possible to seek molecules that interfere with pore formation in order to be later studied as anti-Alzheimer drugs.

Preferably, with no intention to restrict or limit this invention, the procedure herein may be carried out according to the following stages:

Preparation of Pipettes

Preparation of pipettes tubes in order to fix cell membrane starts with the use of "Kwik-Fil"® borosilicate pipettes from World Precision Instruments (WPI). This tube has electric properties, such as lower conductance with regards to other pipettes, and allows for a more accurate measurement of the cells electric resistance.

Pipettes are kept in their original packaging and their ends are polished in an alcohol burner in order to smooth them and increase the electro-physiology equipment life time. Pipettes are placed on a puller which, through heat and pull, allows stretching and cutting the pipette in half, generating two ends with similar properties with an approximate diameter of 1 μm and a resistance of approximately 2-4 MΩ. Pipettes are visually observed in order to determine whether the end is of acceptable characteristics regarding size, uniformity, and cleanliness. This is observed in a Nikon microscope of conventional light transmission and 600× amplification. The equipment where pipettes are pulled and obtained corresponds to a pipette horizontal polisher "Flaming/Brown micropipette puller", model P-87, from Sutter Instrument Company. The protocol is modified according to the desired end conditions. The following protocol applied to ends used in the process described in this invention:

Sutter Instrument Protocol for End Polishing:

At 350 pressure units regarding the P-87 instrument, 6 cycles are used as follows:
    i. Cycle 1: heat 800-pull 102-Speed 50-Time 150
    ii. Cycle 2: heat 795-pull 102-Speed 50-Time 150
    iii. Cycle 3: heat 790-pull 102-Speed 50-Time 150
    iv. Cycle 4: heat 785-pull 102-Speed 50-Time 150
    v. Cycle 5: heat 764-pull 102-Speed 50-Time 150
    vi. Cycle 6: heat 764-pull 102-Speed 50-Time 150

"Heat" are resistance units (A) applied to the filament; "Pull" are weight unit fractions (kilogram); "Speed" is expressed in centimeter/second, and "Time" is expressed in milliseconds.

This protocol is modified according to the operator in order to change the conditions necessary to obtain the desired end. By modifying pull and speed, increasing or decreasing the pipette end diameter and its resistance is possible. Once polishing, pulling, cutting, and microscope inspection processes are completed, pipettes are stored in "Electrode storage rcpt." jars, WPI. Pipettes are stored until their use. Storing them longer than one week is not recommended, as dust and small environmental particles may alter the pipette end, changing its electric properties and the possibility of getting closer to the cell to be studied.

Neuron Cultures

Animals are treated and handled according to the NIH recommendations. 18-day pregnant mice (C57BL7J6) are anesthetized with ether and sacrificed through cervical dislocation. Embryo are quickly removed and beheaded with sterile material. Brains are removed and kept in cold Hank medium.

The midbrain is separated in order to expose the hippocampus area, which is dissected from the brain and mechanically dispersed using trypsin, collagenase, and DNAsa III. Neurons are placed ("planted") in 35 mm dishes covered with poly-L-lisine at a density of 350000 neurons per ml.

Neurons are left to grow in vitro during 12 days, and then recorded using electro-physiology. The means of culture is 80% MEM, 2 mM glutamine, and 10% bovine fetal serum. The means are changed every three days. Every reagent used is dissolved in PBS, which is used as control.

Whole-Cell Patch Clamp

The culture medium in the dish where neurons are cultivated is changed to an external solution containing (in mM): between 100-200, preferably 150 NaCl; 2-10, preferably 5.4 KCl; from 0.5 to 5 preferably 2.0 $CaCl_2$; from 0.1 to 5 preferably 1.0 $MgCl_2$; 1-25 reference 10 glucose, and 1-25 preference 10 HEPES (pH from 7.2 to 7.6 preferably 7.4). The internal solution contains (in mM): 100-220, preferably 120 KCl; from 0.5 to 5, preferably 2.0 $MgCl_2$; from 0.5 to 5, preferably 2 ATP-$Na_2$; 1-25, preferably 10 BAPTA; from 0.1 to 2, preferably 0.5 GTP; 1-25, preferably 10 HEPES (pH 7.4). Cells are stabilized at 18-26° C. temperature, preferably 22° C., at least during 10 minutes, preferably during 30 minutes, before starting the experiments. Resistance changes in cells are detected through the whole-cell patch clamp system (Hamill and col., 1981) and an Axopatch-1D amplifier (Axon Instruments, Inc., Burlingame, Calif.). The visualization system is an inverted microscope (Diaphot, Nikon, Japan) coupled to a fluorescence unit. The membrane potential is adjusted between −50 and −70, preferably at −60 mV. Resistance is recorded at 50 s intervals and filtered at 2-5 kHz using a computer connected to the recording system through an acquisition card (Axon Instruments, Inc.) and computer program pClamp6 (Axon Instruments, Inc.). Solutions for tests are prepared weekly in deionized distillated water kept refrigerated at 4° C.

Peptide Addition

Synthetic peptide Aβ1-40, acquired at TOCRIS or Sigma (USA), which corresponds to the human sequence of β-amyloid peptide (Aβ), is added as follows:

The process starts by dissolving 1 mg commercial peptide in 100 μl DMSO. This solution is proportionally separated in 25 μl amounts in Eppendorf tubes and kept refrigerated at −20° C. This may be kept for 6 months without significantly altering the synthetic peptide properties.

In order to generate the working solution, these portions are defrosted under a laminar flow bell and diluted in sterile PBS at pH 7.4. 700 μl PBS are added to the 25 μl of each peptide portion, obtaining a final work volume of 725 μl, with peptide at an approximate concentration of 100 μM. This peptide solution is defined as "Soluble Peptide" and it is mainly formed by Aβ peptide monomers. This soluble peptide is induced to aggregation by stirring at approximately 600 rpm at temperature around 37° C. During this process, the solution optical density is determined at 405 nm every 15 minutes for a total time of 120 minutes. Measurements are carried out with SmartPec® Plus spectrophotometer from Bio Rad. After 120 minutes, the solution shows an optical density of 0.2-0.3, which indicates that Aβ aggregates were generated. This solution is called "Aggregate Peptide", and electronic microscope inspection has determined that it corresponds to a heterogeneous structure population, among which amorphous aggregate shapes, 100 nm protofibril, and short fibers are noted.

When incubating the peptide for a long time (5 days at 37° C.), a solution cloudy at sight is obtained, mainly formed by long amyloid fibers (longer than 200 nm), as indicated in images obtained under the electronic microscope. We have called this solution "Fibers". The three above described solutions, Soluble, Aggregate, and Fibers, are evaluated according to optical density and electronic microscopy.

Aggregate Electronic Microscopy

Samples are observed under the electronic microscope at 120 kV. Samples are placed on a stand called nickel or copper grate. Different peptide samples (10 μl) are placed on the grate, allowing the material to pour over the grate. Then excess is removed taking care not to stir the material or contaminate the grate with the pouring. Once excess has been removed, the grate is washed during five minutes in distilled water by letting one drop fall on the grate and removing excess the same way the peptide solution was removed.

Then, a uranyl acetate tint at 2% in water solution is carried out, once again letting a drop of this solution fall on the grate, finally removing the excess of uranyl acetate. Grates are left to evaporate on a Petri dish in order to avoid environmental contaminants, such as dust or suspended particles.

Finally, they are placed under the electronic microscope and examined. It is considered that a sample corresponds to the soluble form when no apparent structure is observed in 100 different fields; otherwise, aggregates show organized forms that may correspond to small amorphous structures, protofibril structures (around 100-150 nm long), and short fibers (no longer than 200 nm). Fibril structures longer than 200 nm are considered fibers.

Loading the Pipette End with Aggregates

Peptide aggregates are diluted to working concentration and were made at concentrations from 0.01 μM to 50 μM, preferably between 0.03 and 20, more preferably 0.05 and 10 μM. This aggregate is diluted in an internal solution (called so because it artificially imitates intra-cell fluid) mainly formed by KCl, BAPTA, calcium, and ATP, as previously described. The aggregate is diluted in this solution, which is loaded into the pipette to be used for Patch-Clamp. This solution is taken into a tuberculin syringe, from which the needle has been removed, and a small capillary-HPLC is added. With this modified syringe, the internal solution volume is taken with no Aβ aggregates as control. It may also be used with the aggregate and/or other molecules of biologic interest in the event evaluations and determining the said molecules' pharmacologic activities is required.

Using the capillary-HPLC in the syringe, the internal solution is introduced into the glass pipette, slowly removing it as the pipette becomes full in order to reduce bubbles. The pipette is filled at least three quarters of its length in order to immerse the electro-physiologic equipment recording electrode in the internal solution. Once the capillary-HPLC has been removed and the pipette is full, its sharpest end is carefully knocked in order to remove air bubbles that may have remained and that may alter the equipment electric conduction. Once the pipette is full, it is placed in the electro-physiologic equipment header, from which a silver chloride electrode outstands. The electrode remains inside, in touch with the internal solution. The pipette is fastened to the header, which is placed in a working position that allows handling the pipette (containing the internal solution with the control solutions or Aβ peptide aggregates) to get it close to the cell membrane in a controlled and accurate way.

Performing of Patch-Clamp

Before mounting the pipette, preparing the electro-physiologic system in order to measure changes in electric properties is necessary. The microscope halogen light is turned on, and the cell and the culture dish are placed under the microscope optical focus.

Nitrogen is injected to the working table, the electro-physiologic equipment and the computer that allows information acquisition are turned on. The acquisition program is started; this allows handling the electro-physiologic equipment and acquiring and saving the electro-physiologic information in order to turn it into a digital signal. Once the electro-physiologic system has been started, a reference electrode in introduced in the external solution. This reference electrode is connected to the equipment header and allows forming an electric circuit between the recording electrode, the neurons, the solution, and the reference electrode. With these elements in working position, the pipette is placed in the equipment header prepared with the internal solution, as mentioned above.

Positioning of the Pipette

The electro-physiologic equipment header is manually moved and placed near the cell culture, for which the microscope light is used as a reference. Once the pipette has been centered on the cell culture, this is lowered until it touches the external solution. At that moment, a change is observed in the electro-physiologic equipment, which shows a large voltage difference but, when touching the solution, the different tends to be zero. This change indicates that preparation conditions are correct, and that it is a control point to continue with the procedure.

Following, the pipette shadow is used as a guide for handling. The shadow is observed and, with the help of microhandlers, the pipette is moved in the three header axes until it is close to the cells. When the pipette is over the neuron body, the cell is carefully touched and the seal begins to form. At the moment when the end touches the cell, a change occurs in the electrode resistance.

Forming of Seals and Data Storage

The equipment configuration allows measuring the electric current; therefore, this decreases when the membrane is touched, forming the seal. At the same time, resistance increases from 4 MΩ to tens of GΩ when the cell is touched.

Initially, a current change is observed, as it moves to values near 0 pA. A command is issued in order to generate a 10 mV pulse; with this, a current pulse of variable range according to the pipette resistance is observed in a virtual oscilloscope on the computer screen, whose particularity is being a square pulse. This pulse reflects resistance between the two electrodes.

When touching the cell, the current decreases and the square pulse is significantly reduced in range. This change in the recording instruments shows that the end has touched the membrane and that electric conditions have changed (increase of resistance, to GΩ) as a result of the end contact with the cell membrane.

At this moment, a plastic tube is used, which is connected to the inside of the pipette placed on the header. This allows extracting air from the inside and generating a negative pressure. With this, a highly resistant seal is generated between the membrane and the pipette. In the oscilloscope, this is observed through the disappearance of the square pulse and only two capacitive peaks remain, which primarily represent the pipette capacitive current. At this moment, a cell strongly attached to the pipette is obtained (cell attached, membrane patch). This high resistance values may last 30 or more minutes with normal solution, which is known as "cell-attached". Later, as routine in this invention, the seal status is recorded.

In this invention process, the peptide in its aggregate state is inside the pipette, and no negative pressure is applied to break the membrane. On the other hand, conductance changes in time are recorded, as well as resistance and the membrane electric properties produced by the action of molecules to be studied.

Under these conditions, a change generation on conductance reflects that molecules altered the membrane permeability by perforating it and allowing a small ion flux through these perforations. This way, the methodology shows whether molecules are capable of perforating and altering biologic membranes. As the process positive control, molecules such as gramicidin or other perforating agents are used, already described as capable of altering membranes and changing electric properties.

Data Storage and Analysis

Each data acquisition is carried out with the computer program used by the equipment. These data are stored as .abf files and may be analyzed by the same program. Each oscilloscope screen may be saved as individual or continuous file for later analysis. This program allows analyzing the membrane passive properties, such as resistance and capacitance, in addition to determining the characteristics that describe the capacitive peak, together with calculating the area under it, as a quantitative indicator of the membrane opening.

The invention claimed is:

1. An in vitro electrophysiological procedure to evaluate, in living neural cells, a neuroprotective capacity of an agent of interest in treating amyloid-type diseases, or a neurotoxic capacity of the agent, in real time, wherein the procedure comprises the following steps:
    a) Providing a living cell culture comprising living neural cells;
    b) Generating a seal between plasma membranes of the living neural cells and a patch clamp pipette, conserving a bi-layer integrity;
    c) Exposing the plasma membranes of the neural cells to the agent of interest in treating amyloid diseases, the agent contained in the patch clamp pipette;
    d) Measuring electrophysiological parameters related to plasma membrane integrity wherein results of the measuring are related to formation or non-formation of elemental pores in membranes, and wherein the measuring is carried out in the range of from −40 to −75 pA, after exposing the membrane to said agent of interest; and
    e) Recording the electrophysiological parameters related to the integrity of the membrane.

2. A procedure according to the claim 1, comprising, based on the measuring step, identifying whether the agent of interest is a pharmacologically active molecule or pharmacologically active ingredient useful against neuro-degenerative diseases.

3. The in vitro electrophysiological procedure of claim 1, wherein the agent of interest is selected from the group consisting of peptides, proteins, or pharmacologically active ingredients.

4. An in vitro electrophysiological procedure according to claim 3 wherein the agent of interest is peptide amyloid beta.

5. An in vitro electrophysiological procedure according to claim 4 wherein the peptide amyloid beta concentration is between 0.1 and 1 µM.

6. An in vitro electrophysiological procedure according to claim 1 wherein said measuring step takes place before any indication of calcium influx or membrane de-polarization.

7. The in vitro electrophysiological procedure of claim 1, wherein said electrophysiological parameters related to membrane pore formation are not associated with calcium influx or membrane de-polarization.

8. The in vitro electrophysiological procedure of claim 7, wherein the agent of interest is selected from the group consisting of peptides, proteins, or pharmacologically active ingredients.

9. An in vitro electrophysiological procedure according to claim 1, comprising delivering an intrinsic noise level below 5 pA.

* * * * *